(12) United States Patent
Begin et al.

(10) Patent No.: US 9,174,883 B2
(45) Date of Patent: Nov. 3, 2015

(54) WASTE RECOVERY, CONVERSION, AND UTILIZATION

(75) Inventors: Ryan Begin, North Billerica, MA (US); Shane Eten, Boston, MA (US)

(73) Assignee: FEED RESOURCE RECOVERY, INC., Concord, MA (US)

( * ) Notice: Subject to any disclaimer, the term of this patent is extended or adjusted under 35 U.S.C. 154(b) by 688 days.

(21) Appl. No.: 12/761,849

(22) Filed: Apr. 16, 2010

(65) Prior Publication Data

US 2010/0264079 A1  Oct. 21, 2010

Related U.S. Application Data

(63) Continuation-in-part of application No. 12/424,785, filed on Apr. 16, 2009, now abandoned.

(51) Int. Cl.
| | | |
|---|---|---|
| *C12P 5/00* | (2006.01) | |
| *C12M 1/00* | (2006.01) | |
| *C05F 17/00* | (2006.01) | |
| *C12M 1/107* | (2006.01) | |
| *C12M 1/33* | (2006.01) | |
| *G06Q 10/06* | (2012.01) | |
| *G06Q 99/00* | (2006.01) | |
| *C05F 11/00* | (2006.01) | |
| *C12P 5/02* | (2006.01) | |
| *C02F 3/28* | (2006.01) | |

(52) U.S. Cl.
CPC .............. *C05F 17/00* (2013.01); *C05F 11/00* (2013.01); *C05F 17/0018* (2013.01); *C05F 17/0027* (2013.01); *C12M 21/04* (2013.01); *C12M 29/04* (2013.01); *C12M 43/08* (2013.01); *C12M 45/02* (2013.01); *C12M 45/04* (2013.01); *C12P 5/023* (2013.01); *G06Q 10/06* (2013.01); *G06Q 99/00* (2013.01); *C02F 3/2853* (2013.01); *Y02E 50/343* (2013.01); *Y02W 10/12* (2015.05); *Y02W 30/43* (2015.05); *Y02W 30/47* (2015.05)

(58) Field of Classification Search
CPC ..................................... C12P 5/00; C12M 1/00
See application file for complete search history.

(56) References Cited

U.S. PATENT DOCUMENTS

| | | | |
|---|---|---|---|
| 5,377,917 A | 1/1995 | Wiljan et al. | |
| 6,464,875 B1 * | 10/2002 | Woodruff | 210/603 |
| 2005/0274668 A1 * | 12/2005 | Lee | 210/603 |
| 2007/0095734 A1 * | 5/2007 | Lee, Jr. | 210/180 |
| 2008/0020456 A1 | 1/2008 | Choate et al. | |

FOREIGN PATENT DOCUMENTS

DE   102007051403 A1   4/2008

OTHER PUBLICATIONS

Federman et al. (An Eco-Friendly Waste Disposal Solution for Melba's Restaurant: Final Report. Gateway Design Course, Section 003. Dec. 10, 2007).*
New Hampshire Department of Health and Human Services (Food Processing Plants 2010).*
The Wisconsin Department of Agriculture, Trade and Consumer Protection (Starting a Food Business).*
Fox News (FDA May Expand Recall of Produce From Texas Plant 2010).*
Chang et al., "Membrane Fouling in Membrane Bioreactors for Wastewater Treatment," Journal of Environmental Engineering, Nov. 2002, pp. 1018-1027.
European Supplementary Search Report, EP 10 76 5301, dated Jul. 7, 2014.
Chang, et al., "Membrane Fouling in Membrane Bioreactors for Wastewater Treatment," Journal of Environmental Engineering, Nov. 2002, pp. 1018-1027.
International Search Report and Written Opinion for PCT/US2010/31481 mailed Apr. 16, 2010.

* cited by examiner

*Primary Examiner* — Karen Cochrane Carlson
*Assistant Examiner* — Natalie Moss
(74) *Attorney, Agent, or Firm* — Lando & Anastasi, LLP

(57) ABSTRACT

Food waste streams may be managed efficiently with a waste-processing facility, which in some embodiments may be co-locating a food distribution facility. The waste processing facility includes a pulper fluidly connected to an input configured to receive a heterogeneous waste stream including biodegradable and non-biodegradable components, the pulper configured to mechanically de-fiber the biodegradable component and form a de-fibered biodegradable material, and an anaerobic membrane bioreactor fluidly connected downstream of the pulper and configured to produce biogas and anaerobic effluent from the de-fibered biodegradable material.

7 Claims, 9 Drawing Sheets

DIGESTATE ATTRIBUTES

| | | | |
|---|---|---|---|
| Zn - ZINC | REGULATES CONSUMPTION OF SUGARS | | Zn |
| Mo - MOLYBDENUM | HELPS IN THE USE OF NITROGEN | | Mo |
| Mn - MANGANESE | FUNCTIONS WITH ENZYMES SYSTEMS | | Mn |
| Cl - CHLORIDE | AIDS PLANT METABOLISM | | Cl |
| Fe - IRON | ESSENTIAL FOR FORMATION OF CHLOROPHYLL | | Fe |
| Cu - COPPER | ROOT METABOLISM AND PROTEIN UTILIZATION | | Cu |
| B - BORON | PRODUCTION OF SUGAR AND CARBOHYDRATES | | B |
| S - SULFUR | PROTEIN PRODUCTION, CHLOROPHYLL FORMATION | | S |
| Mg - MAGNESIUM | ESSENTIAL FOR PHOTOSYNTHESIS | | Mg |
| Ca - CALCIUM | STRENGTHEN PLANTS' CELL WALL STRUCTURE | | Ca |
| K - POTASSIUM | BUILDING OF PROTEINS, REDUCTION OF DISEASES | K | K |
| P - PHOSPHOROUS | SOLAR ENERGY INTO CHEMICAL ENERGY | P | P |
| N - NITROGEN | RAPID GROWTH, SEED AND FRUIT PRODUCTION | N | N |
| | | SYNTHETIC | FEED |

FIG. 2B

WASTE RECOVERY, CONVERSION, AND UTILIZATION

RELATED APPLICATIONS

This application is a continuation in part of, and claims the benefit under 35 U.S.C. §120 of U.S. application Ser. No. 12/424,785, titled "WASTE DISTRIBUTION, CONVERSION, AND UTILIZATION," filed on Apr. 16, 2009, which is herein incorporated by reference in its entirety.

TECHNICAL FIELD

In various embodiments, the present disclosure relates to waste recovery and conversion, and more particularly to improved methods and systems for recovering biodegradable waste for conversion into useful products.

BACKGROUND

In nature, plants extract nutrients from the soil to fuel their growth and, if not consumed, decompose into simpler forms of matter (for example, $CO_2$ and soil nutrients), which become energy for the next generation of growing plants. As such, natural organic processes provide a "closed-loop" system of energy and nutrient cycles.

In contrast, in the food industry, waste is abundant. Government studies show that over 40% of the food produced in the U.S. goes to waste, and traditional waste-disposal practices bury over 90% of this waste in landfills, which in turn releases methane, which is more harmful than $CO_2$ as a greenhouse gas. This "cradle-to-grave" system has over-taxed local landfills and has resulted in a growing movement to ban food waste from landfills. In addition, increased disposal site distances, combined with rising energy prices, make transporting waste a costly proposition. This system of waste disposal has also encouraged farmers to purchase increasingly expensive and environmentally harmful chemicals in order to replace soil nutrients lost due to industrial farming practices. The result is an "open-loop" system that does not properly value or recover waste.

SUMMARY

In various embodiments, the present invention relates to systems and methods that use waste-conversion technology to turn previously discarded food waste and other biodegradable waste into fertilizer and/or energy. More particularly, waste-conversion methods can be used to generate energy usable by the waste generator (for example, supermarkets and restaurants) and/or provide a source of affordable fertilizer for local farmers. As a result, economic and environmental value may be recovered from previously discarded waste efficiently and economically.

In one embodiment, there is provided a waste processing system. The system comprises an input configured to receive a heterogeneous waste stream including biodegradable and non-biodegradable components, a pulper fluidly connected to the input, the pulper configured to mechanically de-fiber the biodegradable components of the heterogeneous waste stream to form a de-fibered biodegradable material, and an anaerobic membrane bioreactor fluidly connected downstream of the pulper.

In accordance with one aspect, the system further comprises a separator having an inlet in fluid communication with the pulper and having an outlet in fluid communication with the anaerobic membrane bioreactor.

In accordance with another aspect, the system further comprises a recycling system configured to direct permeate generated from the anaerobic membrane bioreactor to the pulper.

In accordance with another aspect, the system further comprises a solubilization reactor having an input in fluid communication with the pulper and having an outlet in fluid communication with the anaerobic membrane bioreactor.

In accordance with another aspect, the system further comprises a solubilization reactor having an input in fluid communication with the separator and having an outlet in fluid communication with the anaerobic membrane bioreactor.

In accordance with another aspect, the system further comprises a sludge dewatering system having an input fluidly coupled to the anaerobic membrane bioreactor.

In accordance with another aspect, the system further comprises a biogas collector configured to collect biogas produced in the anaerobic membrane bioreactor.

In another embodiment, there is provided a method of processing a waste stream. The method comprises receiving a heterogeneous waste stream including biodegradable waste and non-biodegradable waste at a waste processing facility, separating the biodegradable waste from the non-biodegradable waste, mechanically de-fibering the biodegradable waste at a predetermined temperature in a pulper to form a de-fibered biodegradable waste, and anaerobically digesting the de-fibered biodegradable waste in an anaerobic membrane bioreactor to produce biogas, permeate, and anaerobic effluent.

In accordance with one aspect, the method further comprises using energy generated from the biogas to heat the pulper to the predetermined temperature.

In accordance with another aspect, the method further comprises adjusting a solids loading in the pulper to a predetermined level. In accordance with another aspect, the solids loading of the pulper is adjusted to the predetermined level by recycling liquid extracted from the permeate produced by the anaerobic membrane bioreactor to the pulper.

In accordance with another aspect, the method further comprises solubilizing the de-fibered biodegradable waste in a solubilization reactor prior to anaerobically digesting the de-fibered biodegradable waste.

In another embodiment, there is provided a waste recovery, conversion, and distribution system. The system comprises a food distribution facility, a food retailing facility, and a waste processing facility. The waste processing facility comprises an input configured to receive a heterogeneous waste stream including biodegradable and non-biodegradable components, a separator configured to separate the biodegradable components from the non-biodegradable components, a pulper fluidly connected to the input, the pulper configured to mechanically de-fiber the biodegradable components of the heterogeneous waste stream to form a de-fibered biodegradable material, and an anaerobic membrane bioreactor fluidly connected downstream of the pulper, the anaerobic membrane bioreactor configured to produce biogas and anaerobic effluent from the de-fibered biodegradable material. The waste recovery, conversion, and distribution system further includes a shared transportation infrastructure configured to deliver food from the food distribution facility to the food retailing facility and to deliver the heterogeneous waste stream from the food retailing facility to the waste processing facility.

In accordance with one aspect, of the system, the food distribution facility is co-located with the waste processing facility.

In accordance with another aspect of the system, the shared transportation infrastructure comprises bioaugmented waste shipping containers.

In accordance with another aspect of the system, the waste processing facility is co-located with the food retailing facility.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2B is a table of digestate attributes for materials processed by a biodegradable-waste-processing facility, in accordance with one embodiment;

DESCRIPTION

Figure 1:
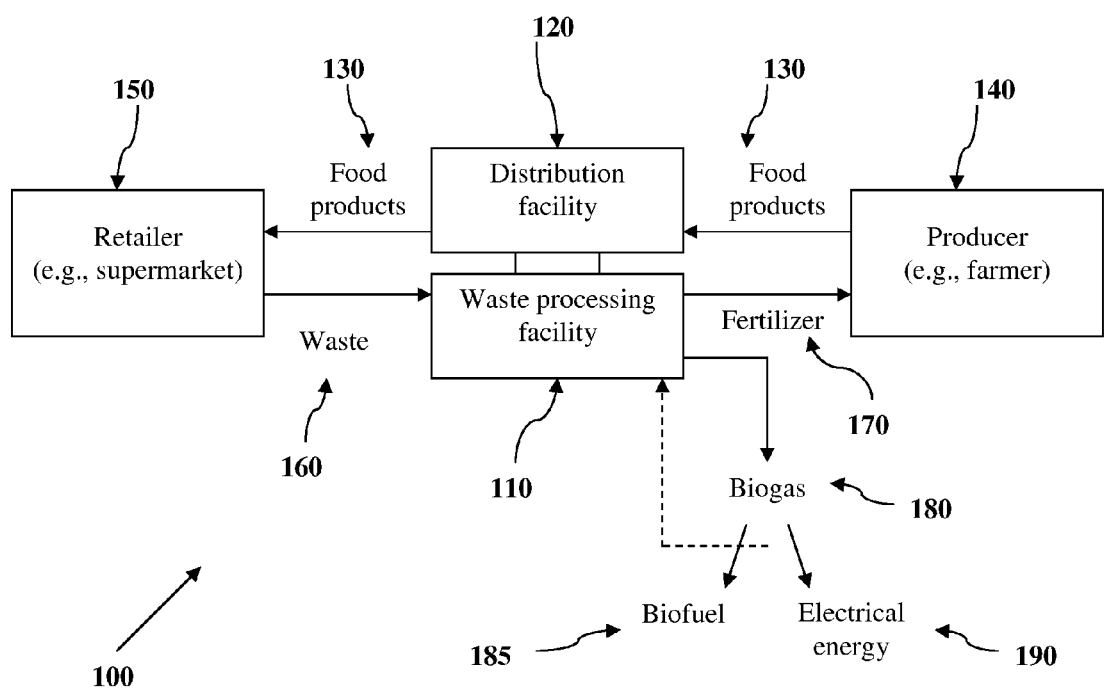
FIG. 1 is a block flow diagram of an exemplary system for distributing food products and collecting and processing heterogeneous waste in accordance with one embodiment.

This invention is not limited in its application to the details of construction and the arrangement of components set forth in the following description or illustrated in the drawings. The invention is capable of other embodiments and of being practiced or of being carried out in various ways. Furthermore, it is to be understood that the features of the various embodiments described herein are not mutually exclusive and can exist in various combinations and permutations. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

In general, the present disclosure relates to the recycling of biodegradable waste to create fertilizer and energy. It allows biodegradable waste generators to turn what was once a liability (for example, food waste to be discarded) into valuable resources. Various embodiments utilize existing transport infrastructure to transport the waste, thus facilitating recycling at little or no additional cost or environmental impact. By integrating waste-conversion technology with existing transport infrastructure, distributed energy generation units, and/or automation and remote management capabilities, certain embodiments provide an all-in-one waste management solution.

Biodegradable waste generators that may benefit from the systems and methods described herein include food retailers, such as supermarkets, food processors, restaurants, and canteens. Slim profit margins, high waste fees, and limited storage space, as well as image consciousness may drive these waste generators to seek clean technology solutions for waste management. Various embodiments of the invention allow them not only to minimize the amount of waste to be disposed of, but also to benefit from waste conversion into fertilizer and renewable energy. Some food waste generators can separate biodegradable from non-biodegradable waste, but at a significant cost, both in time, labor, and money. In various embodiments described herein the need to separate biodegradable from non-biodegradable waste prior to processing is reduced, and in some embodiments, eliminated. Some embodiments disclosed herein enable the processing of heterogeneous waste streams that include both biodegradable and non-biodegradable materials. Non-biodegradable material, as the term is used herein, includes material which biodegrades only slowly, for example, on time-scales which render its processing in a bioreactor unfeasible.

Food retailers are often supplied from a central distribution facility that receives the food products from a producer or wholesaler. Food products, as the term is used herein, includes, but is not limited to, fresh produce such as fruit and vegetables, grains, dairy products, meats, shelf-stable or containerized foods (for example, cartonned, canned, or bagged goods), as well as animal feed. In general, the distribution facility collects the food products from a producer, such as a farmer, wholesale distributor, or food factory, and ships the required quantities of food products to the retailer by truck, freight train, or other appropriate shipping means.

The increased development of central business districts encircled by suburban areas, the increasing mobility of society, and decreased cooking at home have led to significant growth in the commercial food sector, including an increase of commercial areas containing high densities of restaurants, and an increase in ready-to-eat meals sold in supermarkets. As a result, residual fats, oils, and grease (FOG) production through, for example, ware washing, floor cleaning, and equipment sanitation, has increased.

Some embodiments disclosed herein are utilized to dispose of and/or transform into useful products or energy, FOG, which is a by-product that many food service, sales, and generator establishments need to manage. FOG occurs naturally in many foods such as meat. Oil and grease are also incorporated as ingredients into many recipes for bread, salads, and desserts, and are used as a medium for frying food. Thus, FOG is generated as a consequence of cooking.

Sanitary sewer systems are neither designed nor equipped to handle the FOG that accumulates on the interior of the municipal sewer collection system pipes. To prevent FOG from reaching the sanitary sewer, a grease trap or grease separation device may be utilized. A grease separation device is a chamber or underground tank designed to let wastewater pass through, but to retain free or emulsified oil. FOG forms a free-floating layer on the water which can be removed by liquid waste haulers. The material that is collected is often difficult and expensive to dispose of. Providing a central location where supermarkets or their partners can dispose of their FOG may facilitate a reduction in waste management costs as compared with previously practiced methods.

In some embodiments disclosed herein, FOG that was previously disposed of separately from other types of waste can be handled together with the other types of waste. FOG may be blended into a heterogeneous waste stream so as to make up a portion of the chemical oxygen demand (COD) of the waste. This waste is then, in some embodiments, fed into a treatment system. In some embodiments, the treatment system includes an anaerobic digester. In some embodiments, the anaerobic digestion of the waste produces useful materials, such as fertilizer and/or soil amendment and, in other embodiments, biogas, that may be utilized for energy production or processed into other useful products. Biogas typically comprises methane and carbon dioxide as well as small amounts of other gasses such as nitrogen, hydrogen, carbon monoxide, hydrogen sulfide, and/or water vapor. In some embodiments, the waste processing facility may also include an aerobic waste treatment system, for example, a composting system for the production of products such as soil amendment. The synergy created by a central anaerobic digestion facility that handles both heterogeneous waste and FOG serves to consolidate the biodegradable wastes. Moreover, FOG has a significant potential for biogas production.

FIG. 1 illustrates an exemplary system 100 that integrates the delivery of food products to a retailer with the removal of waste from the retailer. The waste treatment facility, in some embodiments, is designed to process both biodegradable and non-biodegradable waste. In some embodiments, waste is provided to the waste treatment facility as a heterogeneous waste stream, including both biodegradable and non-biodegradable waste. In the embodiment of FIG. 1, a waste-processing facility 110, described in more detail below, is located at or near (also referred to herein as "co-located" with) a food product distribution and/or manufacturing facility 120. In some embodiments, the waste processing facility 110 may be located within a same building as the food product distribution and/or manufacturing facility 120. In other embodiments, the waste processing facility 110 may be located within a same industrial park or campus as the food product distribution and/or manufacturing facility 120. In some municipalities, local ordinances may dictate a minimum distance that a waste processing facility 110 must be separated from a food product distribution and/or manufacturing facility 120. Thus, as used herein, for two facilities to be "co-located" means that they are located approximately as physically proximate each other as permitted by applicable ordinances or regulations. In other embodiments, the waste processing facility 110 and the food product distribution and/or manufacturing facility 120 need not be co-located.

In one embodiment, in operation, food products 130 are transported, for example, by rail or truck, from a producer 140 to the distribution and/or manufacturing facility 120 for packaging, processing, and/or distribution to one or more retailers 150. Once the food products have been delivered to a retailer, waste 160 stored by the retailer (including, for example, spoiled and/or unsold produce, packaging material, FOG, non-saleables, and other associated waste), is transported to the waste-processing facility 110. In some embodiments, biodegradable waste is stored by the retailer in a refrigerated or frozen form to limit or prevent decomposition prior to being sent to the waste processing facility 110. In some embodiments, the same transportation infrastructure may be utilized for the delivery of food products from the distribution facility 120 and the return of waste to the waste processing facility 110. As used herein the term "transportation infrastructure" includes vehicles such as rail cars, trucks, or ships, which may be utilized to transport food or waste; the routes, roads, rails, waterways, and the like upon which these vehicles may travel; as well as any containers which may be used to transport the food products or heterogeneous waste. As a result of using the same transportation infrastructure for the delivery of food products from the distribution facility 120 and the return of waste to the waste processing facility 110, in some embodiments, the waste 160 is transported to the waste-processing facility 110 with substantially no additional environmental impact, and little or no additional cost, as this occurs on the return of an existing delivery. In other embodiments, different transportation infrastructures, for example, different sub-sets of a truck fleet are utilized for the delivery of food products 130 and the transportation of waste 160. In some embodiments the same containers are used for both the delivery of food products and the return of heterogeneous waste. For example, if cardboard boxes are used to deliver food products to a retailer, the retailer may use these same cardboard boxes to package biodegradable and/or non-biodegradable waste to be sent to the waste processing facility.

In some embodiments, waste 160 is accumulated by a retailer 150 in containers, which may include portable storage bins delivered to the retailer 150 by a truck during a food product delivery. In other embodiments, dedicated waste containers, which in some embodiments are re-usable or processable with the food waste, are utilized. When these are full, they are collected for return to the waste-processing facility 110, in some embodiments on a return trip of a truck after a subsequent food product delivery. As a result, trucks deliver empty storage bins as part of a regularly scheduled delivery and collect loaded waste-storage bins for return to the waste-processing facility on the return trip. The storage bins may therefore be repeatedly reused as part of the delivery and recycling process. In other embodiments, the storage bins are collected and delivered independently of the delivery of food product. The storage bins may be manufactured from a material or materials including, but not limited to, plastics, metals, cardboard, or other appropriate materials.

In certain embodiments, the waste storage/transport bins are bioaugmented to facilitate pretreatment of the waste in the bins during transport. For example, the bins may contain one or more types of bioaugmentation agents including enzymes, enzyme-secreting fungus (such as *trichoderma reesei*, a mesophilic and filamentous fungus having the capacity to secrete large amounts of cellulolytic enzymes), or other microorganisms. In some embodiments, these bioaugmentation agents begin degrading the organic material within the waste storage/transport bin itself. If different types of waste are stored separately, type-specific pretreatment may be performed. Meat waste may be treated, for example, with lipase enzyme, and produce waste with white-rot fungus or *trichoderma reesei*. In some embodiments, a bioaugmentation agent is manually added to a waste bin when the bin has become full. In other embodiments, a bioaugmentation agent may automatically be released upon the filling of the waste bin. For example, a crushable container made of plastic or other material is present in the waste bin and is crushed open upon a certain weight of material being added to the waste bin, releasing the bioaugmentation agent. In some embodiments, the bins may include vents to allow any gasses generated during the breakdown of the waste within the bin to be released.

Once the waste has been returned to the waste-processing facility 110, the biodegradable fraction can be processed into fertilizer 170 and biogas 180. By co-locating the waste processing facility 110 with the distribution facility 120, waste 160 from multiple retailers 150 can be processed centrally by a single processing facility 110. Furthermore, in some embodiments, because the waste 160 is transported to the distribution facility 120 on the return leg of scheduled deliveries to the retailers, this occurs without incurring additional transport costs.

In some embodiments, the waste-processing facility 110 includes one or more waste-processing units. The waste processing units may include one or more of, for example, pre-screening units, waste de-fibering units, pulpers, systems designed to separate biodegradable from non-biodegradable waste, solubilization reactors, bioreactors, membrane filtration systems, gas collection systems, and fertilizer processing sub-systems. In some embodiments, the waste processing units form more than one waste processing line. Each waste-processing line may include automatic systems that produce fertilizer and energy (for example, biogas) from organic waste, with few or no byproducts. In one embodiment, the waste-processing facility 110 includes a single, stand-alone waste-processing unit. In an alternative embodiment, a number of coupled or separate waste-processing units may be utilized, depending upon the volume of waste being processed and the requirements of the system. Alternatively, different processing units may be linked in series or in parallel to produce the required quantities of fertilizer 170, biofuel 185, which in some embodiments may include processed biogas, and electrical energy 190 for the particular facility.

Fertilizer 170 derived from the biodegradable waste 160 may contain elements, such as micronutrients, that improve soil health and structure and that are not found in synthetic fertilizers. The fertilizer 170, in various embodiments, includes one or more of composted biodegradable waste, processed fertilizer pellets, or liquid fertilizer. In some embodiments, a fertilizer processing system may be co-located with the waste processing facility 110 to process material output from the waste processing facility 110 into a desired form of fertilizer 170. In other embodiment, a fertilizer processing facility is located off site from the waste processing facility 110 and materials produced from the waste processing facility are transported thereto for processing. In further embodiments, materials produced from the waste processing facility 110 are sold directly to consumers or distributers of fertilizer. In some embodiments, the fertilizer 170 generated by the waste-processing unit 110 is distributed to the producers 140 (for example, local farmers) utilizing the same transportation infrastructure that is used to pick up the food products 130 from the producer 140 and deliver it to the distribution facility 120. This allows further exploitation of existing transport infrastructure in delivering the fertilizer 170 to the producer 140 without incurring additional transport costs, and therefore without additional environmental impact. This fertilizer 170 may then be used by the farmer to fertilize crops for subsequent distribution and sale.

In some embodiments, biogas 180 is generated in the waste-processing facility. In some embodiments, this biogas comprises gas formed as a byproduct of the anaerobic digestion of biodegradable waste. In some embodiments, the biogas 180 is collected from an anaerobic digestion system and sold to consumers, packagers, and/or distributors of biogas. In other embodiments, the waste processing facility 110 includes systems capable of converting the biogas to biofuel 185 (in gas, liquid, or solid form) and/or electrical energy 190. In some embodiments, the biofuel 185 is sold to consumers, packagers, and/or distributors of biofuel. The electrical energy 190 is, in some embodiments, used directly to power the waste-processing facility 110. In other embodiments, electrical energy 190 generated by the waste processing facility 110 is distributed through the electrical grid. Heat or other forms of utilizable energy may also be generated by the processing facility 110 in addition to, or in place of, electrical energy.

In an alternative embodiment, a stand-alone waste-processing system is installed at the site of a waste generator (for example, a produce retailer such as a supermarket). The system may be utilized with little operational deviation from current waste-handling practices while allowing the retailer to process the waste directly. In this embodiment, any electrical energy or fuel generated by the processing facility may be utilized directly by the retailer, sold to a distributor or consumer, or distributed through the electrical grid. Fertilizer produced by the waste-processing facility can be delivered to a distributor or a producer of produce through existing transport infrastructure, for example, by shipping the fertilizer to a produce distribution facility using a fleet of trucks also used to deliver produce to the retailer, and/or using a fleet of trucks used to pick up produce from the producer and transport it to the distribution facility. In an alternative embodiment, the retailer can sell the fertilizer directly at its site. The fertilizer is in some embodiments in the form of a soil amendment such as compost which consumers may pick up directly from the retailer. In other embodiments, materials formed in the waste processing system may be further processed, either on site at the retailer, or at a separate facility, into forms such as pelletized or liquid fertilizer.

Use of the systems and methods described herein may create value for users in the form of avoided costs and/or saleable byproducts. The primary avoided costs are, for example, electricity, waste management, depreciation, transportation fuel, and heat. Benefits may also be derived through government-based subsidies such as renewable energy credits (RECs) and carbon credits. Favorable public-relations opportunities may also be gained. In addition, revenue may be created directly through the sale of the fertilizer, electrical energy, and/or fuel produced by the waste processing facility.

Figure 3:
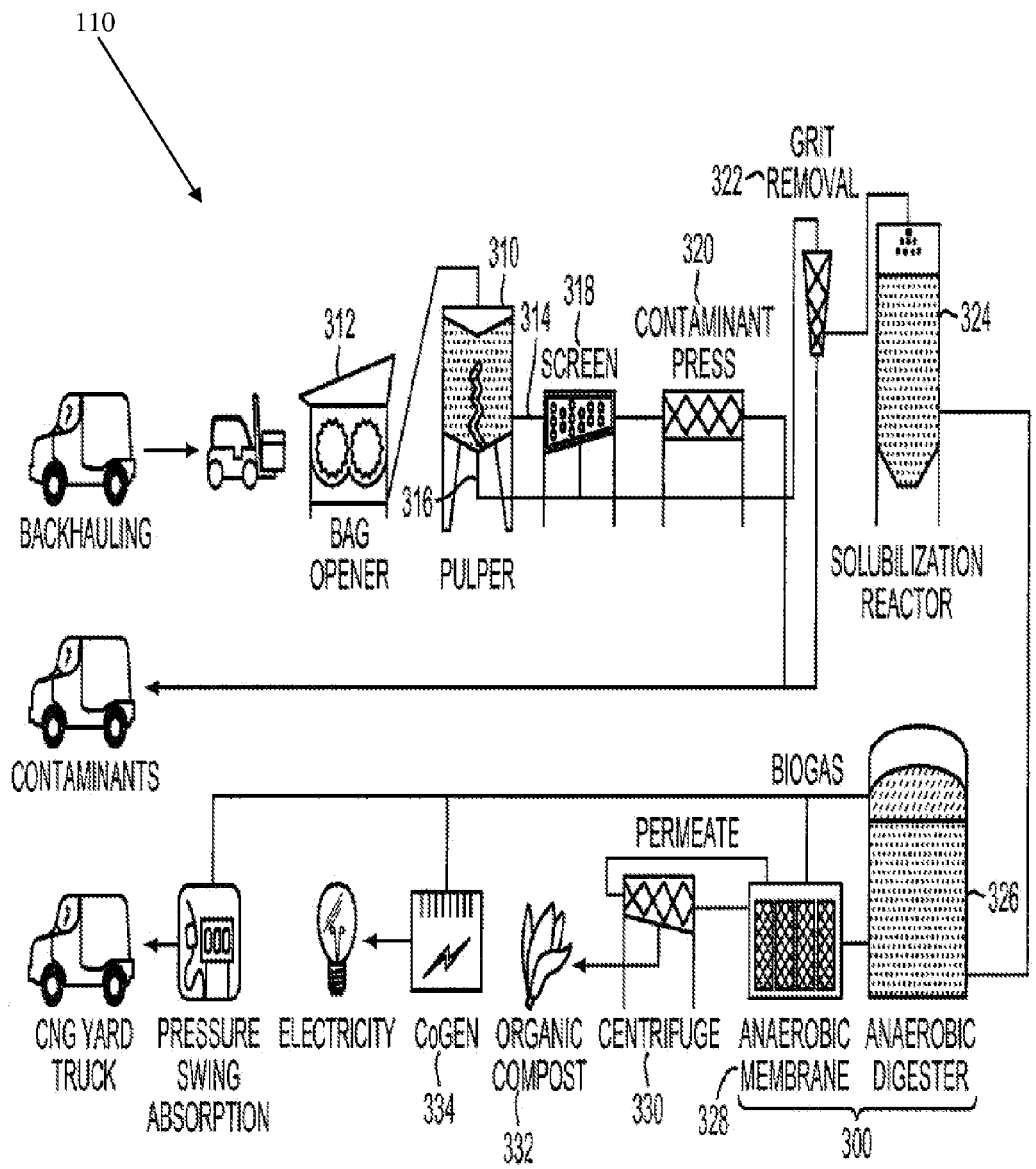
FIG. 3 is a schematic view of a waste-processing facility in accordance with one embodiment.

FIG. 3 depicts a waste processing facility 110 in accordance with one embodiment of the present disclosure. The waste processing facility 110 includes, in some embodiments, apparatus which separates biodegradable from non-biodegradable components. The waste processing facility, in accordance with some embodiments, includes one or more operational units in one or more waste processing lines. These operational units perform operations such as, prescreening waste to be treated, breaking apart containers (for example, cans, bags, or boxes) in which biodegradable waste delivered to the facility is contained, solubilizing waste, removing particulates such as stones, sand, or grit from waste to be treated, mechanically breaking down waste, biologically breaking down waste, and recovering water and/or other liquids from the waste stream. The waste processing facility, in some embodiments, also may include one or more of systems for, for example, producing and capturing biogas from the treated waste, producing heat and/or electricity, and for producing compost and/or fertilizer from the waste.

In some embodiments, the facility 110 includes an input, which may, in some embodiments, include a staging area. In other embodiments, the input to the waste processing facility may comprise a bag opener such as the bag opener 312. In some embodiments, the bag opener 312 is configured to rip plastic and other packaging material, utilizing, for example, weak shear forces, milling, cutting, or any other known mechanism, to release biodegradable waste contained therein. After passing through the bag opener 312, the waste is conveyed to a system for mechanically breaking down the waste, for example a pulper 310, where the biodegradable material is de-fibered. "De-fibering," as used herein, encompasses a process wherein loose molecular bonds in organic materials, such as paper, produce, processed foods, meat, FOG, and the like are mechanically broken such that the material is broken apart into fibrous components.

Figure 4:
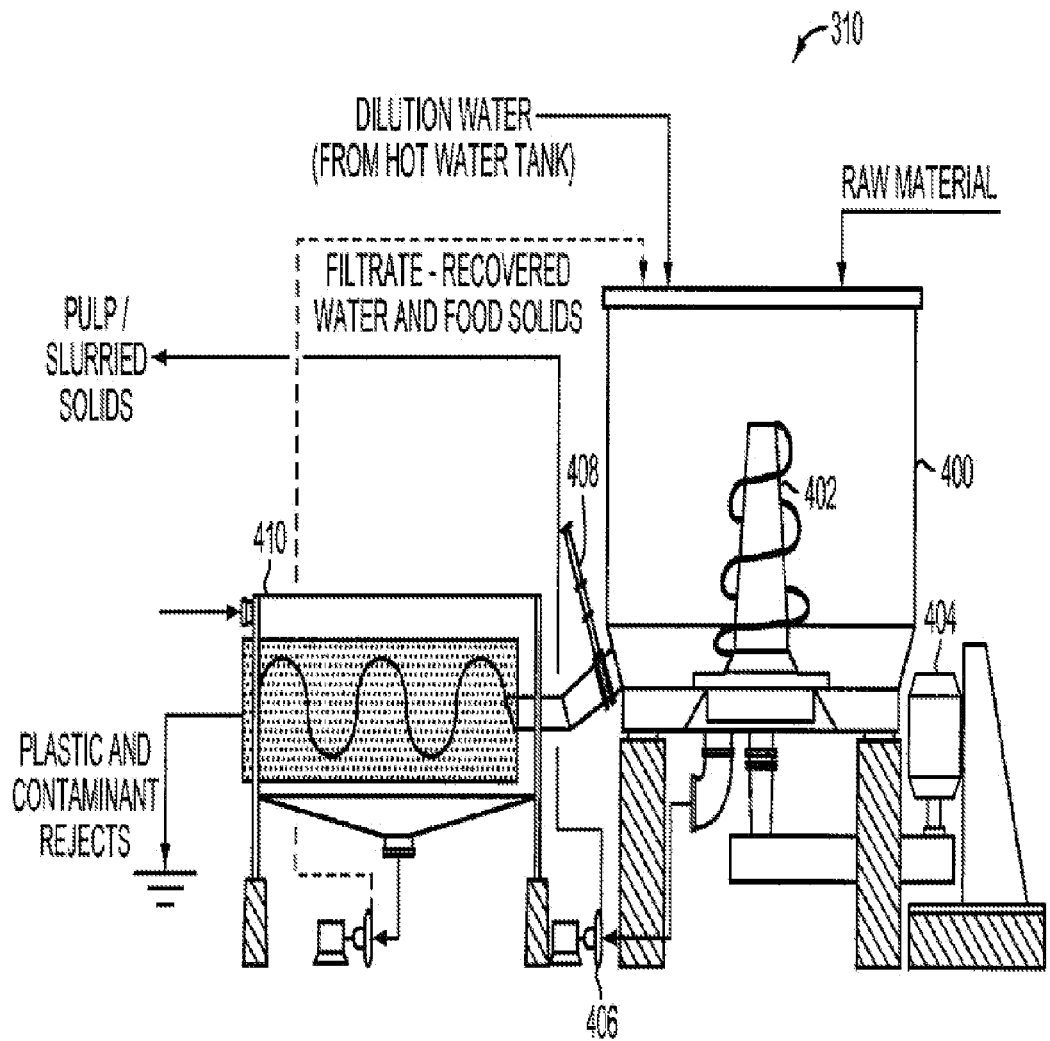
FIG. 4 is a schematic view of a pulper and contaminant removal system in accordance with one embodiment.

FIG. 4 illustrates an exemplary pulper 310 and contaminant removal system. The pulper 310 is used to mechanically break down (or de-fiber) the waste stream delivered from the bag opener into a pulp (a liquid suspension). The pulper, in some embodiments, includes a container into which the heterogeneous waste and a fluid, such as water, are introduced, and a stirring or blending mechanism, such as stiffing blades or a rotor which are used to agitate the heterogeneous waste and fluid in the container. In some embodiments, the pulper 310 may include a tank 400, or stator, for holding the heterogeneous waste feedstock, and one or more rotors 402, for example, one or more helical screw-type rotors, inside the stator for generating hydraulic shear to de-fiber the waste into a pulp. The rotor or rotors are driven by a motor 404. Pulping, as opposed to shredding, the waste largely preserves non-biodegradable waste components while de-fibering the biodegradable material. As a result, the non-biodegradable contaminants are left largely intact and can readily be separated from the pulp suspension. In addition, preserving the structural integrity of these contaminants avoids the release of toxins that could otherwise result from their destruction.

The pulper may process waste in batches or, in some embodiments, continuously. In one embodiment in which the pulper operates in a batch mode, the pulper operates according to the following operational sequence. First, a desired amount of waste is added to the tank 400 along with a fluid, such as hot water which is at a temperature sufficient to facilitate the de-fibering of biodegradable waste in the pulper. The water may, in some embodiments, be heated to between about 110° F. and about 190° F., and in other embodiments, to between about 130° F. and about 170° F. In some embodiments, the water is heated to a temperature of about 150° F. In some embodiments, sufficient waste and fluid are added to the pulper tank 400 to achieve a predetermined solids loading in the tank. The predetermined solids loading is, in some embodiments, determined to provide an acceptable level of operational efficiency of the pulper. For example, in some embodiments, the pulper may operate efficiently with a solids loading of less than about 20% by weight. In other embodiments, this predetermined solids loading is between about 6% and about 16% solids by weight. An optimal solids loading in the pulper may vary based on the design, size, and power of the particular pulper utilized as well as the makeup of the heterogeneous waste to be treated.

After adequate amounts of hot water and raw heterogeneous waste material have been added to the tank 400, the rotor or rotors 402 are turned on, and the pulper is run until the biodegradable material is largely broken down or de-fibered. In some embodiments, the material in the pulper is maintained at a predetermined temperature to facilitate de-fibering of the biodegradable waste during the pulping operation. For example, it has been shown to be effective to maintain the pulper at a temperature in the range of temperatures for the hot water discussed above during operation. Nearly full mechanical breakdown, or de-fibering, of the biodegradable waste may be achieved in, for example, 20 minutes or less, depending on the amount and type of waste being processed. The time to achieve a desired level of breakdown of the biodegradable material varies with the temperature of the pulper, the power of the motor 404, and the speed of operation of the rotor 402. Different degrees of breakdown may be desired depending upon the types of processing operations that are performed downstream from the pulper in different embodiments. In some embodiments, the pulper produces a pulp (a liquid suspension) comprising the de-fibered waste with a solids concentration slightly less than, for example 1% less than the solids concentration of heterogeneous waste and water introduced into the pulper. This is because the non-biodegradable material in the heterogeneous waste stream (that is not included in the pulp) often has a density approaching that of water. In embodiments wherein a significant amount of particularly dense non-biodegradable waste is present in the heterogeneous waste stream, the difference in solids loading between the heterogeneous waste and water mixture introduced into the pulper and the pulp produced would be greater than embodiments in which the heterogeneous waste steam included little and/or less dense non-biodegradable components.

Once the biodegradable material is mechanically hydraulically de-fibered to a desired level, the pulped material is removed from the tank 400 and sent on for downstream processing. In some embodiments, a discharge pump 406 is turned on to allow large fractions of the pulped material to leave the pulper through a perforated bedplate (not shown) located underneath the rotor 402. The bedplate perforations may be of any of multiple different configurations, shapes, and sizes suitable to a particular operation. For example, the bedplate perforations are, in some embodiments, circular, and in other embodiments, elongated, while in other embodiments, the bedplate perforations may be polygon shaped. The bedplate perforations are, in different embodiments, sized differently depending on the type of waste processed. While the pulped material passes through the bedplate, most contaminants are held back due to their size. In some embodiments, the perforations are sized such as to retain non-biodegradable waste within the pulper while allowing the de-fibered biodegradable waste (the pulp) to pass. For example, in embodiments where it is expected that non-biodegradable portions of the heterogeneous waste stream would not be broken into pieces smaller than about an inch in diameter, the bedplate perforations could be sized slightly smaller than an inch in diameter to retain the non-biodegradable components in the pulper tank. In other embodiments, for the processing of food waste from retailers, a bedplate with $3/16$-inch or $1/8$-inch diameter perforations may be used. In other embodiments, the pulped material may leave the pulper tank 400 by a gravity drain, or in some embodiments, using a different transportation mechanism, such as a flat belt conveyor or a screw type conveyor. A screen is used in some embodiments to hold larger portions of the pulped material back from the conveyor and retain these portions in the pulper tank 400. Once a desired amount, for example, a majority, of the pulp suspension has been removed, the remaining pulped material may be diverted to a secondary separator.

To facilitate the process of transporting the remaining pulped material from the pulper tank to the secondary separator, the tank may be refilled with hot water. In some embodiments, hot water is added to the pulper tank until the tank is partially filled, for example, filled up to about a third of its height. Then, a side valve 408 of the pulper tank 400 is opened, and the remaining pulped waste is discharged. Separation hardware 410 (for example, one or more of a rotary sieve, a basket filter, a vibrating screen, a drum screen, or a rotating filter) is used to filter the contaminants, and recycle the water, including any residual pulped biodegradable material, to the pulper. Then, the side valve is closed, and the next batch of waste can be processed. Material that is not broken down by the pulper and/or separation hardware 410 is in some embodiments removed from the separator and disposed of, for example, in a landfill. In some embodiments, the material not broken down by the pulper and/or separation hardware 410 is dewatered prior to disposal. The liquid obtained in this dewatering operation may be reused in, for example, the pulper, or may be sent on for further processing to produce fertilizer, and in some embodiments, purified water, such as water suitable for irrigation or drinking.

Non-biodegradable materials may be subdivided into light and heavy fractions. In some embodiments, a "light fraction" (for example, plastics, waxed cardboard, and/or styrofoam)

and a "heavy fraction" (for example, metal, glass, and/or batteries) of contaminants are moved separately from the pulper. The heavy fraction may be collected. In some embodiments, the collection mechanism may include a flushed trap located on the bottom of the pulper. Rotating scrapers may continuously scrape settled heavy material towards the trap. The trap may be configured with an upper and lower gate, wherein the lower gate includes the bedplate. When the lower gate is closed and the upper gate is open, heavy material is collected in the trap. By flushing the trap with process water, organic build-up may be prevented, and the collected materials cleaned. When the upper gate is closed and the lower gate opened, the heavy waste is discharged from the trap and conveyed to a disposal bin. The light fraction, which primarily contains for example, mixed plastics, foams, and other buoyants, may be captured with a mechanically operated rake submerged into the pulp. Alternatively or additionally, the light waste may be discharged through a side valve, as described above.

With renewed reference to FIG. 3, the pulper 310 may separate a contaminant stream 314 from a suspension of pulped biodegradable waste 316. The contaminants 314 are, in some embodiments, filtered through a screen 318, compacted in a press 320, and shipped off for recycling or disposal. The pulped biodegradable waste 316 is transferred to downstream equipment for further processing. In some embodiments, this downstream equipment includes an anaerobic membrane bioreactor (an AnMBR) 300. Anaerobic digestion is the breakdown of organic material by microorganisms in the absence of oxygen. Although this process occurs naturally in landfills, anaerobic digestion usually refers to an artificially accelerated operation that processes biodegradable waste to produce biogas rich in methane and carbon dioxide, and a digestate which may comprise an anaerobic effluent and/or a stable solid residue.

The suspension of pulped biodegradable material 316 may contain small pieces of sand and grit, which are non-biodegradable and could clog or damage the membrane(s) of the AnMBR 300. In some embodiments, the waste-processing facility may further include a separator such as a grit removal apparatus 322 between the pulper and the AnMBR 300. The grit removal apparatus 322 may, for example, be a hydrocyclone which separates grit from the suspension by centrifugation. Sand and grit are diverted to the bottom of the hydrocyclone, where they fall into a screw conveyor, and are transferred into a container for disposal. In alternate embodiments, one or more other forms of grit removal apparatus may be utilized instead of, or in addition to a hydrocyclone. This grit removal apparatus includes, in some embodiments, one or more of a clarifier, a settling tank, a dissolved air flotation system, and a static filter.

Figures 5A, 5B:
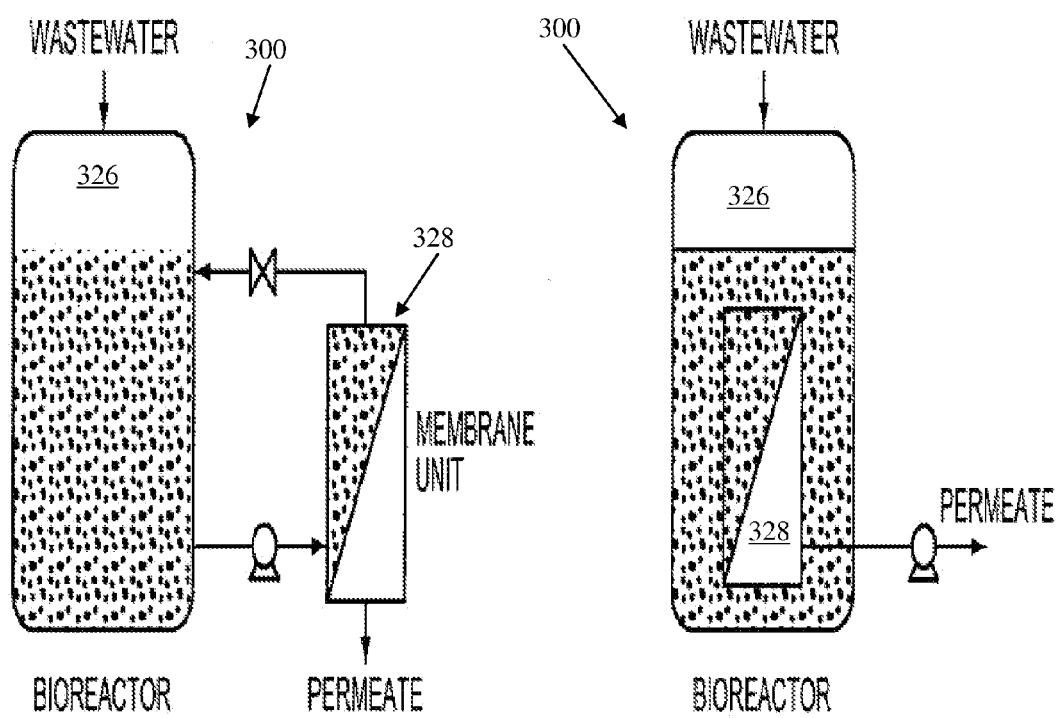
FIGS. 5A and 5B are schematic views of anaerobic membrane bioreactors in accordance with various embodiments.

The grit-free suspension of pulp may be further mechanically or hydraulically solubilized in a solubilization reactor 324, or may instead be directly transferred to the AnMBR 300, depending on the level of disintegration of the material achieved in the pulper. In the AnMBR 300, microorganisms digest the biodegradable pulp into biogas and an anaerobic effluent. The AnMBR 300 includes a bioreactor 326, and a membrane filtration unit 328 submerged in the suspension. The membrane unit 328 performs biomass retention and gas/liquid/solids separation functions. In some embodiments, illustrated in FIGS. 3 and 5A, the membrane unit 328 is separate from the bioreactor 326, requiring the suspension to be pumped through the membrane unit 328. In other embodiments, as illustrated in FIG. 5B, the membrane unit 328 is located inside the bioreactor 326. In some embodiments, the membrane filtration unit 328 uses a flat sheet filtration membrane. In other embodiments, the membrane filtration unit 328 utilizes a plurality of hollow fiber filtration membranes. Other forms of filtration membranes are utilized in different embodiments, and the embodiments of the present disclosure are not limited to any particular type of membrane filtration unit or membrane bioreactor.

Figure 2A:
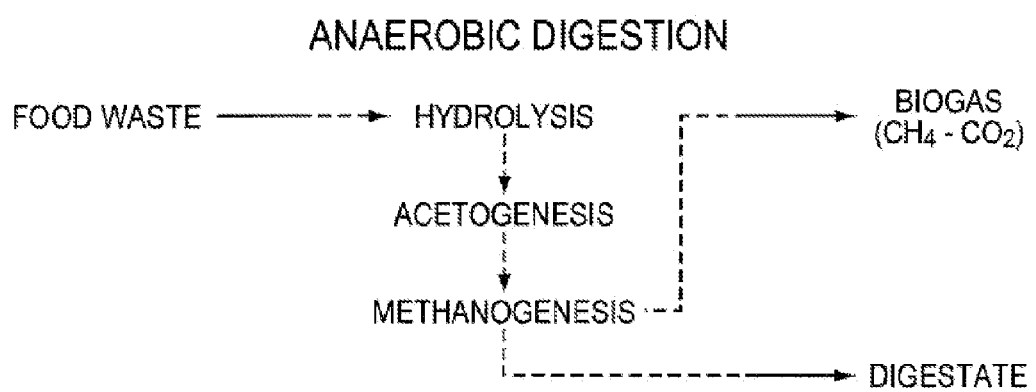
FIG. 2A is a schematic view of an anaerobic digestion process in accordance with one embodiment.

The AnMBR 300 provides for anaerobic digestion of biodegradable waste in the waste stream, which further breaks down the waste stream and in some embodiments, produces valuable by-products. An exemplary anaerobic digestion process for use in a processing facility is shown in FIG. 2A. The digestion process begins with bacterial hydrolysis of the input materials, which breaks down insoluble organic polymers, such as carbohydrates and proteins, and makes them available for other bacteria. Acidogenic bacteria then convert the sugars and amino acids into carbon dioxide, hydrogen, ammonia, and organic acids, and acetogenic bacteria convert the resulting organic acids into acetic acid, along with additional ammonia, hydrogen, and carbon dioxide. Finally, methanogens are able to convert these products to methane and carbon dioxide. The remaining non-digestible material forms the digestate, which is typically rich in nutrients.

FIG. 2B shows a table listing digestate attributes for exemplary materials processed by a biodegradable waste processing facility. As shown in FIG. 2B, synthetic fertilizers typically contain only the mineral nutrients potassium, phosphorous, and nitrogen. In contrast, effluent generated from anaerobically digested biological waste materials includes additional nutrients such as zinc, molybdenum, manganese, chloride, iron, etc. Thus, it can be seen that effluent generated from anaerobically digested biological waste materials may serve as a richer source of mineral nutrients for agricultural applications than traditional synthetic fertilizers.

The success of waste treatment by anaerobic digestions is affected by the effectiveness of biomass retention. Standard reactor designs like continuously stirred reactors (CSTR) and plug-flow reactors (PFR) are susceptible to washout of the microbial mass, and are thus, absent any biomass retention apparatus, generally unsuitable for processing biodegradable waste. For certain wastewaters, biomass retention times can be increased through biomass granulation and/or biofilm formation. These biomass-retaining processes, however, typically work only for narrow ranges of hydraulic flow rates, and suitable concentrations of nutrients and suspended solids.

Anaerobic membrane bioreactors provide alternative means for achieving nearly complete biomass retention, irrespective of the capacity of the biomass to form biofilms of granules, as compared to, for example, an Upflow Anaerobic Sludge Blanket (UASB) reactor. An AnMBR utilizes one or more micro-filtration or ultra-filtration membranes to physically retain biomass inside the reactor, thereby eliminating the risk of biomass washout. More generally, the membrane acts as a filter passing solubilized components, but retaining solids of dimensions greater than a pore size of the membrane(s). As a result, solids retention and hydraulic retention times are decoupled, which increases waste processing performance parameters (for example, a percentage of biodegradable material converted to biogas, a percentage of COD destructed, and/or a methane fraction in biogas). Further, since an AnMBR does not require as much energy for the regeneration of biomass, in contrast to bioreactors that incur substantial biomass losses, it can reach higher overall energy efficiency. In addition, an AnMBR typically has a small footprint, compared with conventional waste-processing bioreactors of the same processing capacity, because of its capacity to handle large organic loading rates.

Anaerobic MBR technology is suitable for high-strength wastewaters, i.e., wastewater with a high biological oxygen demand (BOD). Solid biodegradable waste streams, on the other hand, cannot, in general, be used readily as a feedstock for an AnMBR because the solids would clog the membrane(s) and thus adversely affect the AnMBR performance. Further, solid waste streams are often contaminated by non-degradable or not easily degradable materials such as bone, shells, seeds, pits, glass, metal, plastic, etc. These contaminants can permanently damage the membrane(s), reducing the operational life span of the AnMBR. Further, contaminants in the digestate would preclude use of the digestate as fertilizer.

Various embodiments of the present invention enable the application of anaerobic membrane digestion to contaminated solid (in addition to liquid) waste streams by providing a pulper for the efficient separation of non-degradable contaminants from a mixed waste stream, and the solubilization of the biodegradable material. Mixed waste streams include, for example, food waste mixed with packaging material, municipal waste, industrial waste, and agricultural waste.

The anaerobic digestion process results in two effluent streams: a sludge and a permeate. In some embodiments, the sludge represents a smaller amount of the effluent flow than the permeate. For example, in some embodiments, the sludge represents about 10% of total effluent flow while the permeate represents about 90% of the total effluent flow. The permeate, in some embodiments, has a low suspended solid concentration, but a high concentration of valuable nutrients and minerals. Therefore, it can be further refined to produce a valuable fertilizer as well as reclaimed process water. Process water may be reclaimed from the permeate by use of a membrane filter, or in some embodiments, a reverse osmosis unit, which separates the process water into a filtered liquid and a retentate, the retentate including the nutrients and minerals. The retentate is, in some embodiments, further processed to form a fertilizer. In some embodiments, this further processing takes place in a processing system co-located with the waste processing facility 110, and in other embodiments, takes place at a separate facility. In some embodiments, the reclaimed process water and/or filtered liquid is recycled to the pulper 310. In other embodiments, the filtered liquid is utilized for irrigation, as potable water, and in some embodiments, drinking water.

Water (for example, recycled permeate) which is recycled to the pulper is, in some embodiments, heated by a heat exchanger or otherwise. In other embodiments, the recycled water retains heat which was generated during the biological breakdown of the waste stream in the AnMBR 300. Recycling this heated recycled permeate into the pulper bears the advantage that heat of the permeate is simultaneously transferred to the pulper. If the permeate contains high concentrations of nutrients, such as ammonia, these nutrients may be largely removed from the permeate prior to use of the permeate as process water to avoid toxic levels. Alternatively, the permeate may be used directly as liquid fertilizer and/or irrigation water. Ammonia is toxic to microbes used in anaerobic digestion at concentration of about 3000 mg/l or greater. An ammonia stripper may be employed to reduce ammonia concentrations to about 100 mg/l or less. The ammonia obtained from the permeate may be packaged and sold, or further processed into other chemicals such as fertilizer, which may be sold.

The sludge produced in the AnMBR 300 is, in some embodiments, periodically removed, for example, by a pump or by a gravity drain on a lower section of a retentate portion of the AnMBR. In some embodiments, sludge is removed continuously as it forms in the AnMBR 300. The sludge removed from the AnMBR 300 is, in some embodiments, dewatered. Dewatering of the sludge is performed, in some embodiments, in equipment such as a centrifuge 330. In other embodiments, the sludge is dewatered using a belt filter press, and in other embodiments, is allowed to dry by an evaporative process. In some embodiments, the dewatered sludge is composted to create a soil amendment 312; the extracted water may be added back into the AnMBR, recycled to the pulper 310, or further purified for use in irrigation, potable water, or drinking water applications. In some embodiments, discussed above, the soil amendment may be sold as a fertilizer.

In some embodiments, biogas is produced during the anaerobic digestion of material in the AnMBR 300. In some embodiments, the generated biogas is captured by, for example, a compressor coupled to piping in fluid communication with an internal section of the AnMBR. Mechanisms and apparatus for capturing biogas from AnMBRs is known and is not discussed in detail herein. The biogas has many downstream uses because it is typically comprised of mostly methane. In different embodiments, captured biogas is utilized to produce heat in boilers, to produce electricity and/or heat in fuel cells, turbines, or combined heat and power generators, to produce natural gas for pipeline distribution and resale, or to produce vehicle fuel by cleaning the biogas and compressing it to be dispensed into vehicles that run on compressed natural gas. In some embodiments operations are performed to remove impurities such as moisture, particulates, carbon dioxide, hydrogen, or hydrogen sulfide to further purify the biogas. Once the biogas is purified, it can be compressed and stored to off-set natural gas usage. The biogas generated in the AnMBR 300 is, in one embodiment, converted to electricity and heat in a cogeneration engine 334. The electricity and heat generated is used to power the various pieces of equipment in the waste processing facility. In other embodiments, the biogas is compressed and packaged into gas cylinders. These gas cylinders may be sold, providing an additional source of revenue for the waste processing facility. In further embodiments, the biogas is transmitted by a gas conduit to an offsite power plant or biogas collection facility.

In use, contaminants from the waste stream, and in some embodiments, a biofilm may build up on the membrane(s) of the AnMBR membrane filtration unit 328 over time. These contaminants may, over time, block the pores of the membranes and reduce the filtration efficiency of the AnMBR, requiring a higher trans-membrane pressure to filter the same amount of permeate. Thus, in some embodiments, the AnMBR membrane filtration unit 328 is occasionally cleaned by, for example, backflushing and/or aeration. In some embodiments, a backwash is performed in which one or more of permeate and biogas is periodically directed through the membranes of the AnMBR membrane filtration unit 328 in an opposite direction from that of normal filtration, removing contaminant particles from the membrane pores. In some embodiments, a chemical cleaner, such as citric acid, may be backwashed through the membrane to dissolve accumulated biofilm. In some embodiments, captured biogas may be introduced into the AnMBR to aerate the membranes, removing particles from the surfaces thereof. Piping and valving systems and the operation thereof for performing backwashing and/or aeration of an AnMBR are known and will not be described in detail herein.

In certain embodiments, the waste-processing facility is fully automated, requires little or no maintenance and user training, and enables a user to process waste and generate energy without changing current waste disposal behavior. Automated system management may be readily implemented using conventional equipment and techniques, and may involve the collection of performance data, such as internal pH, biogas production, and nutrient composition of fertilizer product, to assess the operation of the system and determine the necessary adjustments for optimization. For example, a pH-balancing unit may continually adjust the pH of the waste stream, thereby enabling diverse waste handling. In some embodiments, the various sensors are present in the various pieces of equipment utilized in the waste-processing facility. For example, pH sensors may be present in the pulper for determining a waste influent pH, and transmembrane pressure sensor(s) and/or liquid level sensor(s) may be included in the AnMBR 300. These sensors, in some embodiments, feed information into a centralized control system to determine, for example, when and how much pH adjustment to provide to the influent waste stream, and/or when to initiate a cleaning cycle (backwashing and/or aeration) of the AnMBR. In other embodiments, individual pieces of equipment within the waste-processing facility include sensors to measure various parameters of interest and controllers to affect the operation of the equipment.

Figure 6:
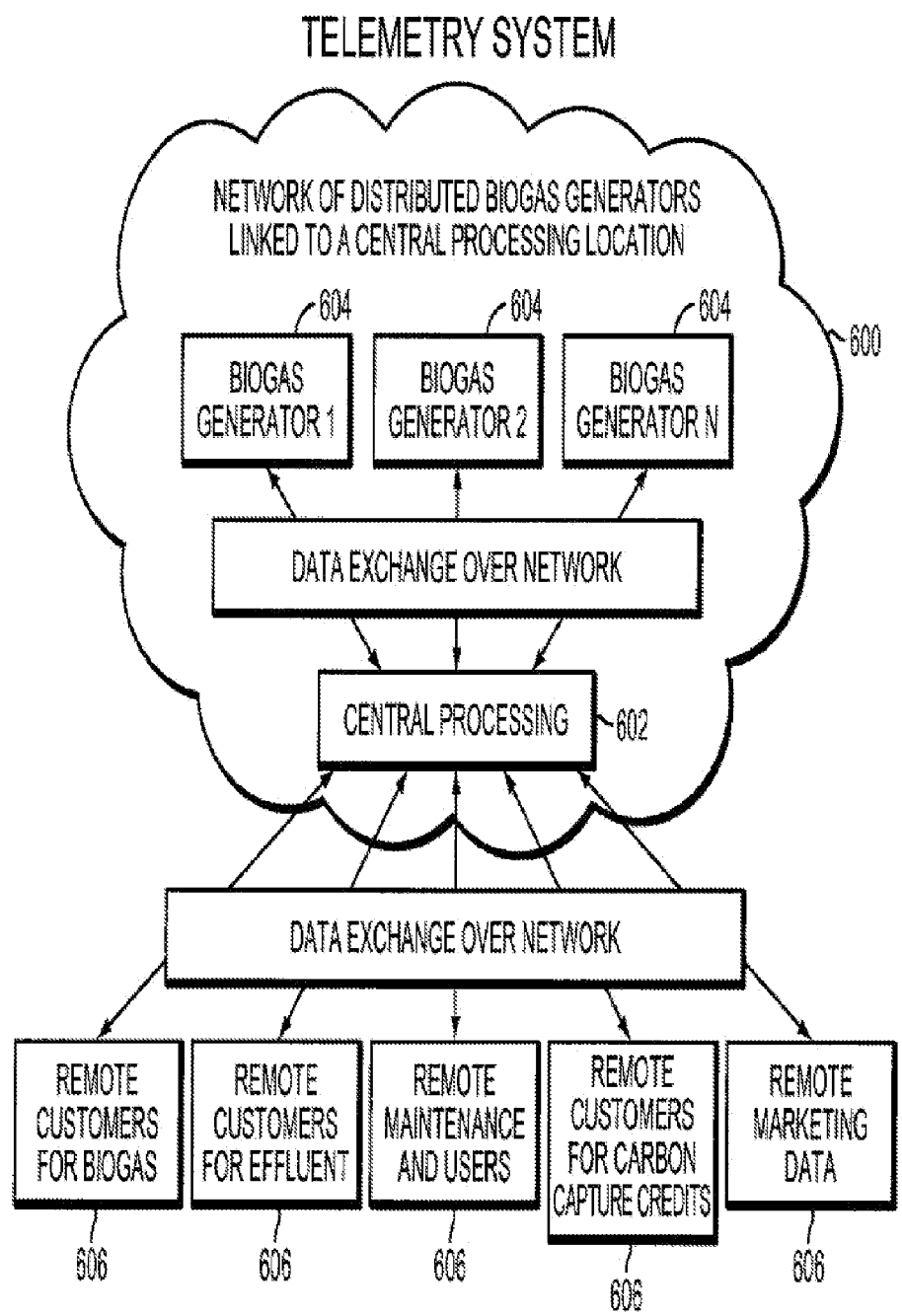
FIG. 6 is a schematic view of a remote telemetry system for a waste-processing facility in accordance with one embodiment.

In some embodiments, the automated management of the processing facility facilitates its remote control. In some embodiments, the waste processing includes multiple integrated biogas generator units (each having at least an AnMBR) for increased flexibility and reliability, and is an enclosed system remotely managed by a telemetry system, as illustrated for exemplary purposes in FIG. 6. The telemetry system 600 may include a central processing module 602 in communication with the biogas generator units 604. The central processing module 602 monitors the quality of byproducts and overall system performance, allowing it to quickly identify irregularities and diagnose malfunctions. The central processing module 602 may also give customers 606 access to critical data relevant to the performance of the system. Data that may be monitored includes, for example, daily and total waste amounts, waste by category, energy of input wastes, and waste disposal and processing trends. Managing the data remotely may result in a number of benefits for users, such as, but not limited to, waste savings, energy savings, public relations benefits, environmental, calculations, networked system management, improved operational performance, waste stream and efficiency analysis, and capacity management. For example, using the telemetry system 600, multiple processing facilities located at multiple distribution facilities may be monitored from a single remote location, allowing for efficient control and maintenance of a number of facilities with minimal input from the day-to-day users of the processing units. In some embodiments, the telemetry system 600 may comprise a SCADA (Supervisory Control and Data Acquisition) system.

In different embodiments, a monitoring computer or controller for monitoring parameters from various sensors within any one or more of the pieces of processing equipment in the waste processing facility 110 may be embodied in any of numerous forms. The monitoring computer or controller may receive feedback from sensors such as pressure, temperature, pH, chemical concentration, or liquid level sensors in any one or more of, for example, the bag opener 312, the pulper 310, the grit remover 322, the solubilization reactor 324, the membrane bioreactor 300, the centrifuge 330, or other pieces of equipment in the waste processing facility 110. In some embodiments the monitoring computer or controller produces an output for an operator, and in other embodiments, adjusts processing parameters for equipment in the waste processing facility, based on the feedback from these sensors.

Figure 7:
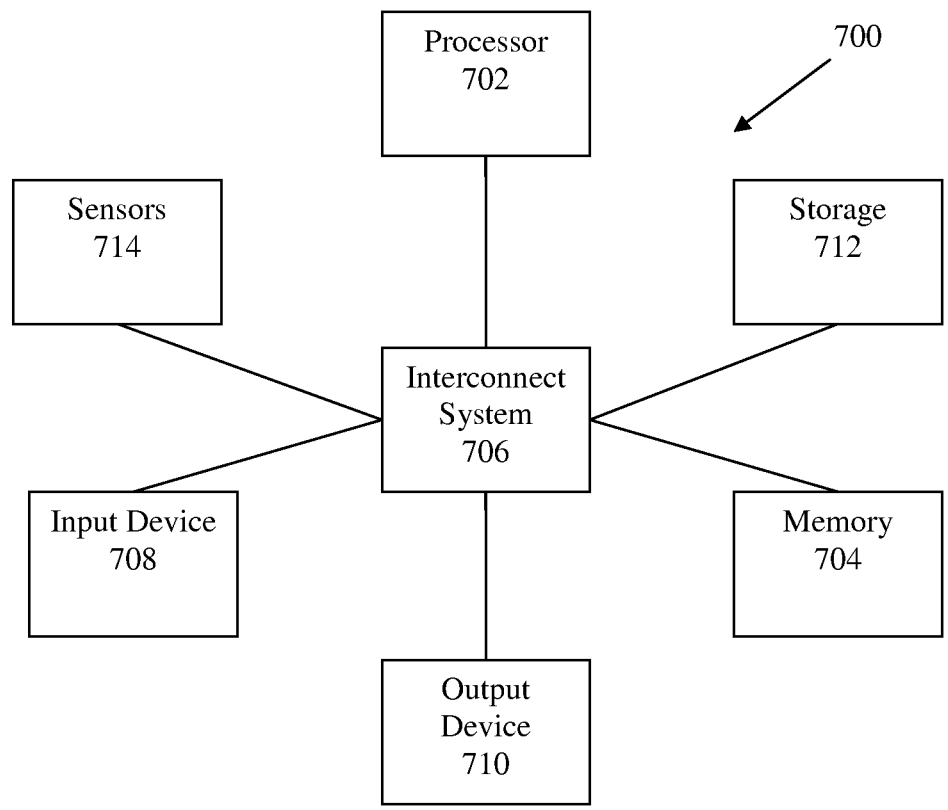
FIG. 7 illustrates a computerized control system which may be utilized in one or more embodiments.

In one example, a computerized controller for embodiments of the system disclosed herein is implemented using one or more computer systems 700 as exemplarily shown in FIG. 7. Computer system 700 may be, for example, a general-purpose computer such as those based on an Intel PENTIUM® or Core™ processor, a Motorola PowerPC® processor, a Sun UltraSPARC® processor, a Hewlett-Packard PA-RISC® processor, or any other type of processor or combinations thereof. Alternatively, the computer system may include specially-programmed, special-purpose hardware, for example, an application-specific integrated circuit (ASIC) or controllers intended specifically for semiconductor wafer processing equipment.

Computer system 700 can include one or more processors 702 typically connected to one or more memory devices 704, which can comprise, for example, any one or more of a disk drive memory, a flash memory device, a RAM memory device, or other device for storing data. Memory 704 is typically used for storing programs and data during operation of the controller and/or computer system 700. For example, memory 704 may be used for storing historical data relating to measured parameters from any of various sensors within any of the equipment in the waste processing facility over a period of time, as well as current sensor measurement data. Software, including programming code that implements embodiments of the invention, can be stored on a computer readable and/or writeable nonvolatile recording medium (discussed further with respect to FIG. 8), and then copied into memory 704 wherein it can then be executed by processor 702. Such programming code may be written in any of a plurality of programming languages, for example, Java, Visual Basic, C, C#, or C++, Fortran, Pascal, Eiffel, Basic, COBAL, or any of a variety of combinations thereof.

Components of computer system 700 may be coupled by an interconnection mechanism 706, which may include one or more busses (e.g., between components that are integrated within a same device) and/or a network (e.g., between components that reside on separate discrete devices). The interconnection mechanism typically enables communications (for example, data and/or instructions) to be exchanged between components of system 700.

The computer system 700 can also include one or more input devices 708, for example, a keyboard, mouse, trackball, microphone, touch screen, and one or more output devices 710, for example, a printing device, display screen, or speaker. The computer system 700 may be linked, electronically or otherwise, to one or more sensors 714, which, as discussed above, may comprise, for example, sensors such as pressure, temperature, pH, chemical concentration, or liquid level sensors in any one or more of, for example, the bag opener 312, the pulper 310, the grit remover 322, the solubilization reactor 324, the membrane bioreactor 300, the centrifuge 330, or other pieces of equipment in the waste processing facility 110. In addition, computer system 700 may contain one or more interfaces (not shown) that can connect computer system 700 to a communication network (in addition or as an alternative to the network that may be formed by one or more of the components of system 700). This communications network, in some embodiments, forms a portion of a process control system for the waste processing facility.

According to one or more embodiments, the one or more output devices 710 are coupled to another computer system or component so as to communicate with computer system 700 over a communication network. Such a configuration permits one sensor to be located at a significant distance from another sensor or allow any sensor to be located at a significant distance from any subsystem and/or the controller, while still providing data therebetween.

Figure 8:
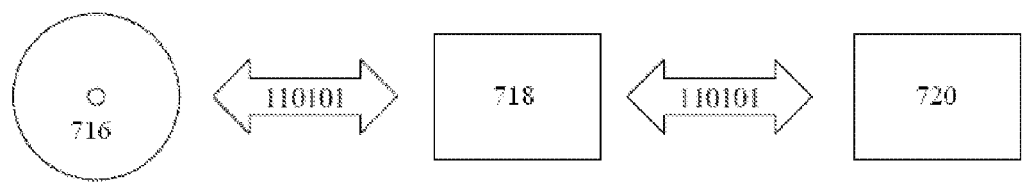
FIG. 8 illustrates a storage system that may be used with the computerized control system of FIG. 7 in accordance with one or more embodiments.

As exemplarily shown in FIG. 8, controller/computer system 700 can include one or more computer storage media such as readable and/or writeable nonvolatile recording medium 716 in which signals can be stored that define a program to be executed by one or more processors 720 (such as processor 702). Medium 716 may, for example, be a disk or flash memory. In typical operation, processor 720 can cause data, such as code that implements one or more embodiments of the invention, to be read from storage medium 716 into a memory 718 that allows for faster access to the information by the one or more processors than does medium 716. Memory 718 is typically a volatile, random access memory such as a dynamic random access memory (DRAM) or static memory (SRAM) or other suitable devices that facilitates information transfer to and from processor 720.

Although the computer system 700 is shown by way of example as one type of computer system upon which various aspects of the invention may be practiced, it should be appreciated that the various embodiments of the invention are not limited to being implemented in software, or on the computer system as exemplarily shown. Indeed, rather than implemented on, for example, a general purpose computer system, the controller, or components or subsections thereof, may alternatively be implemented as a dedicated system or as a dedicated programmable logic controller (PLC) or in a distributed control system. Further, it should be appreciated that one or more features or aspects of the control system may be implemented in software, hardware or firmware, or any combination thereof. For example, one or more segments of an algorithm executable on the computer system 700 can be performed in separate computers, which in turn, can be in communication through one or more networks.

EXAMPLES

The following examples provide comparisons between embodiments of the apparatus and methods disclosed herein and selected previously known apparatus and previously practiced methods.

Example 1

Comparison of Food Waste Management Methodologies

A supermarket waste stream typically includes as much as 80% heterogeneous food waste. The food that is discarded is largely edible but not saleable. The following example compares three different methodologies for management of food waste. To analyze the different methodologies, a hypothetical grocery distribution center that services 200 stores will be considered.

Method 1—Distributed Waste Collection/Off-Site Processing

One waste management model currently in use is to collect heterogeneous food waste over a distributed area and then haul that material to a regional off-site processing facility. The waste management model under this example includes the use of individual trash trucks to haul waste away from each supermarket to a regional landfill, anaerobic digester, or composting site. The amount of fuel required to transport material from the store to regional landfills is cost prohibitive and unable to be controlled by the supermarket. Recycling of food waste through composting or anaerobic digestion in this scenario is not cost effective. It was observed that it is very difficult to collect enough food waste within a local region to produce the economies of scale which would enable an anaerobic digester or composter to operate efficiently. Table 1 below details the costs associated with this method:

TABLE 1

| Method 1 - Distributed/Off-Site | |
|---|---|
| # of Supermarkets (SM) | 200 |
| Food waste per SM per day | 675 lbs* |
| Cost per ton of waste | $115** |
| Annual cost per store | $14,167 |
| Annual cost for all stores | $2.8 million |

*Average food waste per day as reported from a representative sample of supermarkets throughout the United States.
**Cost per ton of waste as reported by a representative sample of supermarkets in Maine, Massachusetts, and New Hampshire which operate in accordance with this method.

Method 2—Centralized Waste Collection/Off-Site Processing

Several southern California based supermarket chains backhaul heterogeneous food waste on a daily basis back to their distribution center. The same trucks that deliver groceries to the supermarkets from the distribution center haul the food waste back from the supermarkets to the distribution center. This provides the supermarkets an opportunity to control food waste costs from one centralized location rather than a distributed model, as in Method 1. For a specific supermarket, the centralized model slightly reduces waste costs, but there is still a large fee to pay for the material to be trucked off-site from the distribution center. In one supermarket chain, once the material is collected, it is then trucked over 140 miles to a compost site. Although this allows the composter to collect enough material to generate the economies of scale which allow for efficient treatment operation, it still requires multiple trucking runs to drive the material to an off-site processing facility. There is a high cost associated with hauling the material off-site and still does not allow the supermarkets to control their waste costs. Table 2 below details the costs associated with this method:

TABLE 2

| Method 2 - Centralized/Off-Site | |
|---|---|
| # of Supermarkets (SM) | 200 |
| Food waste per SM per day | 675 lbs |
| Cost per ton of waste | $90*** |
| Annual cost per store | $11,087 |
| Annual cost for all stores | $2.2 million |

***Cost per ton of waste as reported from a southern California supermarket chain operating in accordance with this method.

Method 3—Centralized Waste Collection/On-Site Processing

Using existing distribution routes to collect and back haul heterogeneous food waste to distribution centers helps reduce trucking costs but does not allow the supermarket to control their cost or utilize the food waste. There are no existing processes or tools to allow a supermarket to process their own waste or to capture the value that their waste contains. Processes, as disclosed herein, which include centralized waste collection and processing in a facility co-located with a food distribution facility allows the heterogeneous food waste to be converted into renewable energy on-site. The energy that can be generated from the food waste back hauled to a standard supermarket distribution center can satisfy over 20% of the distribution center's entire energy demand, equal to over one megawatt of renewable power. The space required for this system has been calculated to be less than 40,000 square feet. It has been calculated that this system would consume a parasitic load of less than 15% of the total power generated. Table 3 below details the costs associated with this method:

TABLE 3

| Method 3 - Centralized/On-Site | |
|---|---|
| # of Supermarkets (SM) | 200 |
| Food waste per SM per day | 675 lbs |
| Cost per ton of waste | $0 |
| Annual cost per store | $0 |
| Annual cost for all stores | $0 |
| Avoided waste costs | $2.2 million |
| Annual Energy produced | 74,460 MMBtu |
| Annual Energy value @$10/MMBtu | $0.74 million |
| Total annual cost savings | $2.94 million |

Example 2

Comparison of Anaerobic Digestion Technologies

The following example compares the suitability of several forms of commercially available anaerobic digestion systems for use on a site co-located with a hypothetical food distribution center serving 200 supermarkets.

To treat food waste on-site, space constraints and commercially available technology must be considered. Composting on-site is typically not a viable option due to the large amount of required space for windrows. Using celluslosic ethanol conversion technology has limited to no success with supermarket waste because of the heterogeneous mix of biodegradable and non-biodegradable materials typically included therein. Treating food waste with incineration technologies like pyrolysis and gasification is difficult and energy intensive because of the high water content in food waste. One viable option involves anaerobic digestion of the food waste, which has shown to be an efficient and cost effective method to treat food waste.

To make on-site anaerobic digestion treatment possible several conditions are considered, including:
1. On-site space constraints—small foot print preferred; and
2. Production of low COD, BOD and TSS wastewater—efficient digestion process preferred.

To satisfy these conditions, a high rate anaerobic digestion process may be used. Anaerobic digestion technology varies by different types of materials and configurations. The general types of anaerobic digesters when treating food waste for 200 supermarkets at a total 24,637 tons per year of food waste can be classified as in Table 4 below:

TABLE 4

| Type | Footprint | | Effluent Quality**** | | | On-Site |
|------|-----------|--|----------------------|--|--|---------|
| | OLR (g-l/d) | Calculated Tank Size (gal) | COD (g/l) | BOD (g/l) | TSS (g/l) | Option (y/n) |
| Lagoon | 1.1 | 5.29 million | 81-93.5 | 59-68.4 | 23-25.2 | N |
| Plug Flow | 1.4 | 4.16 million | 78-86.7 | 36-42.7 | 22.3-24 | N |
| Continuously Stirred Reactor | 2.2 | 2.65 million | 62.6-77 | 29.8-35.4 | 21.5-26 | N |
| Up Flow Anaerobic Sludge Blanket | 5.5 | 1.06 million | 35.9-46.7 | 16-23.1 | 8.8-11.9 | N |
| Anaerobic Membrane Bioreactor | 8.5 | 0.69 million | 2-3.3 | 1.1-1.8 | <.04 | Y |

****In the above table, values for COD, BOD, and TSS for the Lagoon and AnMBR methods were calculated based on typical organic destruction rates for these methods. The values of these parameters for the Plug Flow, Continuously Stirred Reactor, and Up Flow Anaerobic Sludge Blanket methods were obtained from testing by the inventors of the present application.

Each anaerobic digestion technology has benefits and drawbacks. As mentioned above, important factors for having an on-site anaerobic digester are the footprint and effluent quality.

The volume of the tank required to contain the anaerobic digestion process is calculated using the systems organic loading rate (OLR). The units of OLR are how many grams of COD can be treated per day per liter of reactor volume. To determine the total reactor volume, and thus the footprint, the total grams of COD to be treated per day must be calculated. To determine the total grams of COD from 200 supermarkets, the total amount of food waste and the density of the food waste must be considered. With an average of 675 pounds per store per day and the nominal case of 200 stores, a centralized system located on-site must treat 135,000 pounds (61,235 kilograms) per day. Supermarket food waste typically has a density of about 0.9 liters per kilogram, equating 61,235 kilograms to 55,112 liters. Given that average supermarket food waste has a COD of about 400 grams per liter, there is 22,044,600 grams of COD that must be treated per day.

To have an anaerobic digester work on-site within a commercial or industrial type setting the effluent generated by the system should be treatable using conventional means. In some applications, it may be desirable that liquid produced from the anaerobic digestion process be clean enough to be discharged into an existing sanitary sewer or a surface discharge. Permit restrictions in most areas will not allow for the discharge of high COD, BOD, or total suspended solids (TSS) effluents into sanitary sewers or surfaces. Taking space constraints and effluent quality restrictions that many facilities would be subject to into considerations leads to the conclusion that a desirable solution for anaerobic digestion on-site includes AnMBR technology.

Example 3

Material Preparation

The following example describes the testing and comparison of two different methods for producing a liquid solution suitable for anaerobic treatment in a membrane bioreactor from supermarket waste: shredding and pulping.

There are some significant challenges for using AnMBR technology with solid food waste. The first challenge with an AnMBR is to liquefy waste to be treated because the bioreactor typically functions optimally when the material to be treated is in a purely liquid form. The second challenge is to remove contamination or grit from the material to be treated before the material is introduced into the AnMBR so that this contamination or grit does not damage the membrane(s) of the AnMBR. Supermarket waste is typically collected in a solid form contaminated with plastic, glass, metal, bone fragments, and other difficult to remove materials. Supermarket waste would thus preferably be pre-treated to form a liquid suspension prior to introduction into an AnMBR.

Shredding Trial

One processing technology used in anaerobic digestion systems to reduce the size of food waste is a shredder. For this test a shredder was used in series with a ribbon blender. The shredder reduced the initial food waste in size and the ribbon blender helped homogenize the feedstock. A Shred-Tech ST-10™ shredder with a 10 horsepower electric motor (Shred-Tech, Cambridge, Ontario) was tested to breakdown supermarket heterogeneous food waste into a maximum particle size of ¾ inch. The shredded food waste was then mixed in a Ross™ 15 cubic foot dual ribbon blender (Charles Ross & Son Company, Hauppauge, N.Y.) with hot water at 120° F. to further mechanically break the food waste into smaller particles. 125 pounds of supermarket food waste containing fruits, vegetables, meat, deli meats, and bakery and dairy items was feed into the shredder. The exact food waste contents and weights are illustrated in Table 5 below.

TABLE 5

Shredding Trial Food Waste

| Deli (lbs) | | Produce (lbs) | | Greens (lbs) | | Meat (lbs) | | Bakery (lbs) | |
|---|---|---|---|---|---|---|---|---|---|
| Meat | 2.5 | Apples | 18.4 | Greens | 4.7 | Trimmings | 16.2 | Donuts | 6.2 |
| Chicken | 1.7 | Bananas | 7.9 | Lettuce | 23.8 | Beef | 3.5 | Cake | 5.4 |
| Meals | 1.7 | Potatoes | 9.8 | Flowers | 1.3 | Chicken | 2.3 | Breads | 4.2 |
| Deli meat | 1.3 | Tomatoes | 8.6 | | | Pork | 1.2 | Fillings | 0.3 |
| Cheese | 0.8 | Onions | 3.2 | | | | | | |

The current draw on the shredder was 19.5 amps and it took approximately 35 minutes of cumulative time to shred the 125 pounds of food waste. The shredder frequently stalled due to contaminants in the waste stream. The time required to clear shredder jams is not captured in the minutes. The 125 pounds of shredded food waste was then put into the ribbon blender with 20 gallons water at a temperature of 120° F. The ribbon blender mixed for approximately 20 minutes with an average current draw of 4.2 amps. The processed food waste was extracted from the ribbon blender and screened with a ¼" filter. Approximately 80 pounds of material did not pass through the screen. The total solids of the screened material was 22% as compared to the total solids of the food waste, which was 30%. The total pounds of solids shredded was 37.5 pounds, and the total pounds of solids that did not pass through the filter after treatment was 17.6 pounds. This resulted in a total efficiency of 53.1% of the material passing through the screen. The liquid material that passed through the screen was of low quality. This was presumably due to the shredding action breaking large contaminants into smaller particles, which allowed the contaminants to pass through the screen. The energy required to process the food waste through the shredder and ribbon blender was 4.725-kilowatt hours and 0.575-kilowatt hours respectively. The calculated energy required to process a ton of food waste with the shredder is, therefore, 84.8-kilowatt hours.

Pulping Trial

A two cubic meter pulper (custom made from Kadant Black Clawson, Inc., Mason, Ohio) with a 7.5 horsepower motor was tested to break down supermarket food waste into a liquid waste stream. 125 pounds of supermarket food waste containing fruits, vegetables, meat, deli, bakery and dairy was feed into the shredder. The exact food waste contents and weights are illustrated in Table 6 below.

TABLE 6

Pulping Trial Food Waste

| Deli (lbs) | | Produce (lbs) | | Greens (lbs) | | Meat (lbs) | | Bakery (lbs) | |
|---|---|---|---|---|---|---|---|---|---|
| Meat | 2.3 | Apples | 18.2 | Greens | 5.0 | Trimmings | 16.2 | Donuts | 6.0 |
| Chicken | 1.6 | Bananas | 8.1 | Lettuce | 23.5 | Beef | 3.3 | Cake | 5.5 |
| Meals | 1.8 | Potatoes | 9.7 | Flowers | 1.2 | Chicken | 2.4 | Breads | 4.1 |
| Deli meat | 1.5 | Tomatoes | 8.6 | | | Pork | 1.3 | Fillings | 0.3 |
| Cheese | 0.9 | Onions | 3.5 | | | | | | |

The pulper was filled with 15 gallons of 120° F. water and 75 pounds of heterogeneous food waste. The pulper was then run for eight minutes. The average current draw during the eight minute period was 12 amps. The remaining 50 pounds of food waste and an additional 10 gallons of 120° F. water was added to the pulper. The pulper was turned back on for eight additional minutes. The average current draw during the second eight minute period was 6.8 amps. It was observed that the meat, deli, and bakery waste had liquefied well. The contaminants remained largely intact, including the bone and skin that had been separated from the meat. The pulper was run for an additional four minutes with the current draw holding at 6.8 amps. The processed food waste was extracted from the pulper and screened with a ¼" filter. Approximately 4.7 pounds of material did not pass through the screen. The total solids of the screened material was 20% as compared to the total solids of the food waste, which was 30%. The total solids of the food waste was 37.5 pounds and the total solids of the material that did not pass through the filter after treatment was 0.93 pounds. This resulted in a total efficiency of 97.5% of the material passing through the screen. The energy required to process the food waste through the pulper was 1.22-kilowatt hours. The calculated energy required to process a ton of food waste with the pulper is, therefore, 19.5-kilowatt hours.

A comparison of the two process technologies demonstrates that shredding and ribbon blending food waste are not effective in pre-treating food waste for downstream use in an AnMBR. The material produced with a pulper is ideal for an AnMBR due to the ability to keep contaminants largely intact and produce small, hard to separate, particles. Furthermore, the pulper is roughly four times as efficient as the shredder and ribbon blender combination in breaking down food waste, as illustrated in Table 7 below.

TABLE 7

| Processing Technology | kWh per Ton of food waste | Separation Efficiency |
|---|---|---|
| Shred/Ribbon Blender | 84.8 kWhs | 53.1% |
| Pulper | 19.5 kWhs | 97.5% |

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A waste recovery, conversion, and distribution system comprising:
 a food supplier, a food product distribution facility, a plurality of food retailers, a waste processing facility, a transportation vehicle comprising a food product storage container and a separate waste storage bin;

wherein the food product distribution facility receives food products from the food supplier;

wherein the plurality of food retailers receive food products from the food product distribution facility and provide organic waste food product to the waste processing facility;

wherein the food products are delivered to the plurality of food retailers and the organic waste food product is delivered to the waste processing facility by the transportation vehicle;

wherein the waste storage bin has been pretreated with one of an enzyme and a microorganism capable of degrading organic waste food product, and wherein the organic waste food product produced at the food retailer is placed into the waste storage bin;

wherein the waste processing facility is co-located with the food product distribution facility;

wherein the waste processing facility comprises an anaerobic bioreactor configured to produce biogas from the organic waste food product; and wherein the biogas is converted to energy and the energy is used as an energy source at the food product distribution facility.

2. The waste recovery, conversion, and distribution system of claim 1, further comprising a cogeneration engine configured to convert the biogas into the energy.

3. The waste recovery, conversion, and distribution system of claim 1, wherein the waste processing facility comprises an anaerobic membrane bioreactor and an ammonia stripper configured to obtain ammonia from a permeate generated from the anaerobic membrane bioreactor.

4. The waste recovery, conversion, and distribution system of claim 1, wherein the waste processing facility further comprises a pulper fluidly connected upstream of the anaerobic bioreactor.

5. The waste recovery, conversion, and distribution system of claim 1, wherein the food supplier includes one or more of a food processor, a food producer, a farmer, a wholesaler, and a food factory.

6. The waste recovery, conversion, and distribution system of claim 1, wherein the plurality of food retailers include a plurality of supermarkets.

7. The waste recovery, conversion, and distribution system of claim 4, wherein the waste processing facility further comprises a solubilization reactor having an input in fluid communication with the pulper and having an outlet in fluid communication with the anaerobic bioreactor.

* * * * *

UNITED STATES PATENT AND TRADEMARK OFFICE
CERTIFICATE OF CORRECTION

| | |
|---|---|
| PATENT NO. | : 9,174,883 B2 |
| APPLICATION NO. | : 12/761849 |
| DATED | : November 3, 2015 |
| INVENTOR(S) | : Ryan Begin et al. |

Page 1 of 1

It is certified that error appears in the above-identified patent and that said Letters Patent is hereby corrected as shown below:

In the Specification:

At Column 9, line number 2, delete "stiffing" and insert --stirring--.

At Column 21, line number 16, insert --35-- between "the" and "minutes".

Signed and Sealed this
Ninth Day of August, 2016

Michelle K. Lee
*Director of the United States Patent and Trademark Office*